(12) United States Patent
Loesel et al.

(10) Patent No.: US 8,740,888 B2
(45) Date of Patent: *Jun. 3, 2014

(54) COMPUTER CONTROL FOR BIO-MECHANICAL ALTERATION OF THE CORNEA

(75) Inventors: Frieder Loesel, Mannheim (DE); Josef F. Bille, Heidelberg (DE); Luis Antonio Ruiz, Bogotá (CO)

(73) Assignee: Technolas Perfect Vision GmbH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/016,558

(22) Filed: Jan. 18, 2008

(65) Prior Publication Data

US 2009/0187171 A1    Jul. 23, 2009

(51) Int. Cl.
*A61B 18/20* (2006.01)

(52) U.S. Cl.
USPC ............... 606/5; 606/4; 606/10; 128/898

(58) Field of Classification Search
USPC .................................. 128/898; 606/4–5, 10
See application file for complete search history.

(56) References Cited

U.S. PATENT DOCUMENTS

| | | | |
|---|---|---|---|
| 4,665,913 A | 5/1987 | L'Esperance, Jr. | |
| 4,669,466 A | 6/1987 | L'Esperance | |
| 4,718,418 A | 1/1988 | L'Esperance, Jr. | |
| 4,887,592 A | 12/1989 | Loertscher | |
| 4,907,586 A * | 3/1990 | Bille et al. ................ | 606/5 |
| 5,281,211 A | 1/1994 | Parel et al. | |
| 5,425,727 A | 6/1995 | Koziol | |
| 5,993,438 A * | 11/1999 | Juhasz et al. .............. | 606/5 |
| 6,110,166 A | 8/2000 | Juhasz | |
| 6,325,792 B1 * | 12/2001 | Swinger et al. ............ | 606/4 |
| 6,610,051 B2 | 8/2003 | Bille | |
| 6,887,232 B2 | 5/2005 | Bille | |
| 2003/0212387 A1 * | 11/2003 | Kurtz et al. ............... | 606/4 |
| 2004/0044355 A1 | 3/2004 | Nevyas | |
| 2004/0243111 A1 | 12/2004 | Bendett et al. | |
| 2005/0107773 A1 * | 5/2005 | Bergt et al. ............... | 606/4 |
| 2005/0113813 A1 * | 5/2005 | Bille ......................... | 606/5 |
| 2006/0106372 A1 * | 5/2006 | Kuhn et al. ............... | 606/5 |
| 2007/0179483 A1 | 8/2007 | Muhlhoff et al. | |

FOREIGN PATENT DOCUMENTS

| | | | |
|---|---|---|---|
| EP | 0209992 A | 1/1987 | |
| WO | 9409849 A | 5/1994 | |

\* cited by examiner

*Primary Examiner* — Bill Thomson
*Assistant Examiner* — Jeffrey Lipitz
(74) *Attorney, Agent, or Firm* — Nydegger & Associates

(57) ABSTRACT

A system and method for altering the shape of a lamina of transparent material (e.g. the cornea of an eye), as it is being subjected to a transverse pressure differential, requires a computer controlled laser unit. In accordance with specified input parameters, the computer directs the laser unit to perform LIOB over predetermined surfaces within the lamina. This weakens the material for a desired reshaping of the lamina in response to the pressure differential. With respect to a perpendicular axis that is defined by the lamina, surfaces parallel to the axis (e.g. cylindrical surfaces) are separated from each other by about two hundred microns. For surfaces perpendicular to the axis, the separation is about ten microns. In each instance, the cuts that result from LIOB are only about two microns thick.

20 Claims, 3 Drawing Sheets

COMPUTER CONTROL FOR BIO-MECHANICAL ALTERATION OF THE CORNEA

FIELD OF THE INVENTION

The present invention pertains generally to systems and methods for reshaping a transparent material that is being subjected to a transverse pressure differential. More particularly, the present invention pertains to systems and methods for performing cuts on predetermined surfaces inside the material, to thereby weaken the material and allow it to be reshaped in response to the pressure differential. The present invention is particularly, but not exclusively, useful for systems and methods that correct the vision of patients by weakening stromal tissue in the cornea of an eye, to allow intraocular pressure in the eye to reshape the cornea under the influence of bio-mechanical forces.

BACKGROUND OF THE INVENTION

The cornea of an eye has five (5) different identifiable layers of tissue. Proceeding in a posterior direction from the anterior surface of the cornea, these layers are: the epithelium; Bowman's capsule (membrane); the stroma; Descemet's membrane; and the endothelium. Behind the cornea is an aqueous-containing space called the anterior chamber. Importantly, pressure from the aqueous in the anterior chamber acts on the cornea with bio-mechanical consequences. Specifically, the aqueous in the anterior chamber of the eye exerts an intraocular pressure against the cornea. This creates stresses and strains that place the cornea under tension.

Structurally, the cornea of the eye has a thickness (T), that extends between the epithelium and the endothelium. Typically, "T" is approximately five hundred microns (T=500 µm). From a bio-mechanical perspective, Bowman's capsule and the stroma are the most important layers of the cornea. Within the cornea, Bowman's capsule is a relatively thin layer (e.g. 20 to 30 µm) that is located below the epithelium, within the anterior one hundred microns of the cornea. The stroma then comprises almost all of the remaining four hundred microns in the cornea. Further, the tissue of Bowman's capsule creates a relatively strong, elastic membrane that effectively resists forces in tension. On the other hand, the stroma comprises relatively weak connective tissue.

Bio-mechanically, Bowman's capsule and the stroma are both significantly influenced by the intraocular pressure that is exerted against the cornea by aqueous in the anterior chamber. In particular, this pressure is transferred from the anterior chamber, and through the stroma, to Bowman's membrane. It is known that how these forces are transmitted through the stroma will affect the shape of the cornea. Thus, by disrupting forces between interconnective tissue in the stroma, the overall force distribution in the cornea can be altered. Consequently, this altered force distribution will then act against Bowman's capsule. In response, the shape of Bowman's capsule is changed, and due to the elasticity and strength of Bowman's capsule, this change will directly influence the shape of the cornea. With this in mind, and as intended for the present invention, refractive surgery is accomplished by making cuts on predetermined surfaces in the stroma to induce a redistribution of bio-mechanical forces that will reshape the cornea.

It is well known that all of the different tissues of the cornea are susceptible to Laser Induced Optical Breakdown (LIOB). Further, it is known that different tissues will respond differently to a laser beam, and that the orientation of tissue being subjected to LIOB may also affect how the tissue reacts to LIOB. With this in mind, the stroma needs to be specifically considered.

The stroma essentially comprises many lamellae that extend substantially parallel to the anterior surface of the eye. In the stroma, the lamellae are bonded together by a glue-like tissue that is inherently weaker than the lamellae themselves. Consequently, LIOB over layers parallel to the lamellae can be performed with less energy (e.g. 0.8 µJ) than the energy required for the LIOB over cuts that are oriented perpendicular to the lamellae (e.g. 1.2 µJ). It will be appreciated by the skilled artisan, however, that these energy levels are only exemplary. If tighter focusing optics can be used, the required energy levels will be appropriately lower. In any event, depending on the desired result, it may be desirable to make only cuts in the stroma. On the other hand, for some procedures it may be more desirable to make a combination of cuts and layers.

As will be appreciated by the skilled artisan, transparent materials that can be altered by LIOB are susceptible to being weakened by the process. Further, if the material is formed as a lamina (i.e. it is essentially a layer of material), and if the material is subjected to a transverse pressure differential, the lamina can be reshaped when it is weakened by LIOB. In particular, the lamina will be influenced by a change in the force distribution that results from an alteration of the transverse pressure differential that is caused by selective LIOB. Under this influence, the lamina is reshaped. Thus, in a manner similar to the situation disclosed above for a reshaping of the cornea, a lamina, or layer, of transparent material can be similarly reshaped.

In light of the above, it is an object of the present invention to provide systems and methods for reshaping a layer of transparent material when the material is being subjected to a transverse pressure differential. Another object of the present invention is to provide computer-controlled methods for performing laser procedures on transparent material that require minimal destruction of the material. Yet another object of the present invention is to provide computer-controlled methods for altering the shape of a lamina of transparent material that are relatively easy to implement and comparatively cost effective.

SUMMARY OF THE INVENTION

In accordance with the present invention, a system and method for altering the shape of a transparent lamina (e.g. the cornea of an eye) requires a computer-controlled laser unit. More specifically, reshaping of the lamina is accomplished by causing Laser Induced Optical Breakdown (LIOB) on predetermined surfaces within the material, while the lamina is being subjected to a transverse pressure differential. In response to this weakening, the consequent rearrangement of the force distribution within the material will then reshape the lamina. In the specific case of ophthalmic laser surgery in the cornea, the transverse pressure differential is created by intraocular pressure from aqueous in the anterior chamber of the eye.

For a preferred embodiment of the present invention, a computer is electronically connected to a laser unit. With this connection, the system first identifies an axis that is substantially perpendicular to the lamina. For ophthalmic laser surgery, this axis will be the visual axis of the eye. In any event, identification of the axis is important for the purpose of establishing a reference datum that can be used to direct the laser beam that is generated by the laser unit along predetermined paths in the transparent material (cornea).

In operation, the laser beam is focused to a focal spot in the lamina, and the focal spot is then moved in accordance with a predetermined computer program. The purpose here is to perform Laser Induced Optical Breakdown (LIOB) on a defined surface inside the material. For one type of operation, the surface will be oriented substantially parallel to the axis. For another, the surface will be created substantially perpendicular to the axis. In the former case (i.e. when the surface is parallel to the axis) the cuts that result from LIOB may be made either on a curved cylindrical surface (i.e. cylindrical cuts), or on a flat radial surface (i.e. radial cuts). The exact nature and extent of these cuts will, of course, depend on the particular cut parameters that are input to the computer. In the latter case (i.e. when the surface is perpendicular to the axis) LIOB will create so-called "layer cuts". Thus, in overview, the present invention envisions cylindrical cuts, radial cuts and layer cuts.

For cylindrical cuts (circular or oval), and for radial cuts, the cut parameters that are input to the computer include a location for a distal end of the surface $(Z_{distal})_n$. In the notation "$(Z_{distal})_n$,", the letter "n" represents a number from 1 to "n" that identifies the particular surface. In addition to $(Z_{distal})_n$, the cut parameters also include a location for a proximal end of the surface $(Z_{proximal})_n$, a radius "$r_n$" measured from the axis, and an azimuthal angle "θ" measured around the axis from a base line.

Using the cut parameters, radial cuts result from the specific case wherein the azimuthal angle "θ" is constant. The radius "$r_n$" can then be varied through a range of approximately three millimeters. On the other hand, for cylindrical cuts the radius "$r_n$" can either be constant (to create circular cylindrical cuts), or varied along an elliptical path (to create oval cylindrical cuts). Importantly, with both the cylindrical cuts and the radial cuts a plurality of surfaces may be specified. Further, it is very important that each cylindrical surface be centered on the axis, with respective cylindrical surfaces preferably separated from each other by approximately two hundred microns. For both cylindrical and radial cuts, each cut preferably has a thickness of approximately two microns.

As indicated above, the present invention also envisions creating layer cuts that are oriented substantially perpendicular to the axis. Like the cylindrical and radial cuts, layer cuts are created by selectively moving the focal spot in accordance with the predetermined computer program. As is done for the cut parameters, layer parameters that define portions of the layer for LIOB need to be input to the computer.

For layer cuts, the layer parameters include an axial location for each layer $Z_m$ wherein "m" identifies the particular layer. The layer parameters also include an inner diameter $(d_i)_m$, an outer diameter $(d_o)_m$, and an azimuthal angle θ measured around the axis from a base line. The result in this case is the LIOB of material on a plurality of annular shaped layers within the lamina (cornea). Note: when the inner diameter is zero (i.e. $(d_i)_m=0$) the layer cut will actually be disk shaped. Importantly, like cylindrical cuts, each layer is centered on the axis. Similar to the cylindrical and radial cuts, the LIOB of the material for layer cuts results in a layer having a thickness of approximately two microns. Unlike cylindrical cuts, however, when a plurality of layers is created, adjacent layers are only about ten microns distant from each other.

When the system and methods of the present invention are used for ophthalmic laser surgery, it is important that the cylindrical cuts, radial cuts and layer cuts, if made, need to be confined within an operational volume. Specifically, this operational volume is confined within the stroma and extends from just below Bowman's capsule (e.g. approximately 8 microns below Bowman's) to a depth equal to about ninety percent of the cornea (e.g. to about four hundred and fifty microns below the anterior surface of the eye). Further, the operational volume extends in the stroma through a radial distance of about four millimeters. It will be appreciated that the actual boundaries of the operational volume may vary slightly. Importantly, however, LIOB should not occur in Bowman's capsule, nor should LIOB extend into the anterior chamber of the eye.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
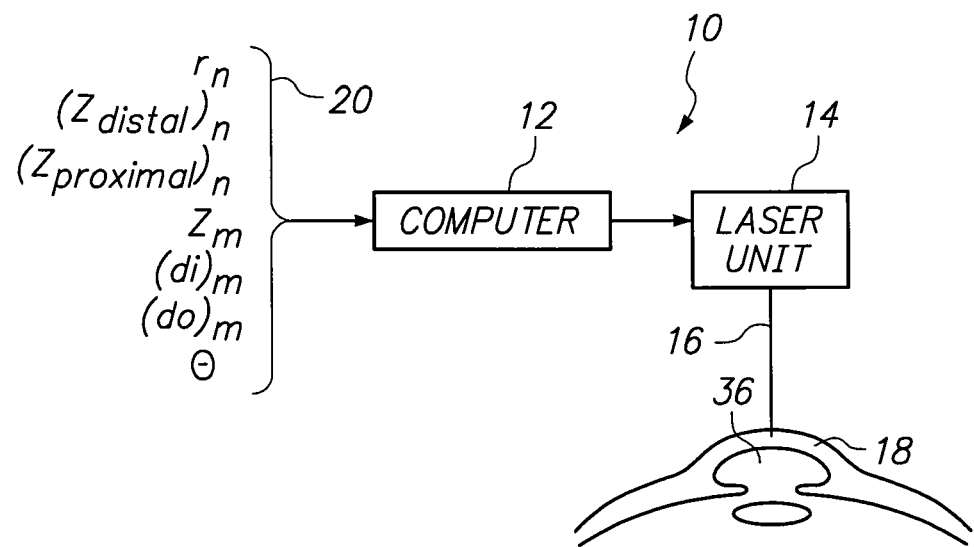
FIG. 1 is a schematic presentation of the system of the present invention shown in relation with the cornea of an eye.

Referring initially to FIG. 1, an ophthalmic laser system in accordance with the present invention is shown, and is generally designated 10. As shown, the system 10 includes a computer 12 that is electronically connected to a laser unit 14. For the present invention, the laser unit 14 is intended to direct a laser beam along a beam path 16, for focus of the laser beam at focal points inside the cornea 18 of an eye of a patient (not shown). It is envisioned that the laser beam will be a so-called "femtosecond" laser, and that the laser unit 14 will be capable of generating a sequence of laser pulses, wherein each pulse in the sequence has a duration that is less than approximately one picosecond. Further, it is envisioned that the laser unit 14 includes optics that will focus the "femtosecond" laser to focal spots in the cornea 18 for Laser Induced Optical Breakdown (LIOB) of tissue in the cornea 18. According to the present invention, the computer 12 is used to control operation of the laser unit 14, and this operation will be consistent with specified input parameters 20.

Figure 2:
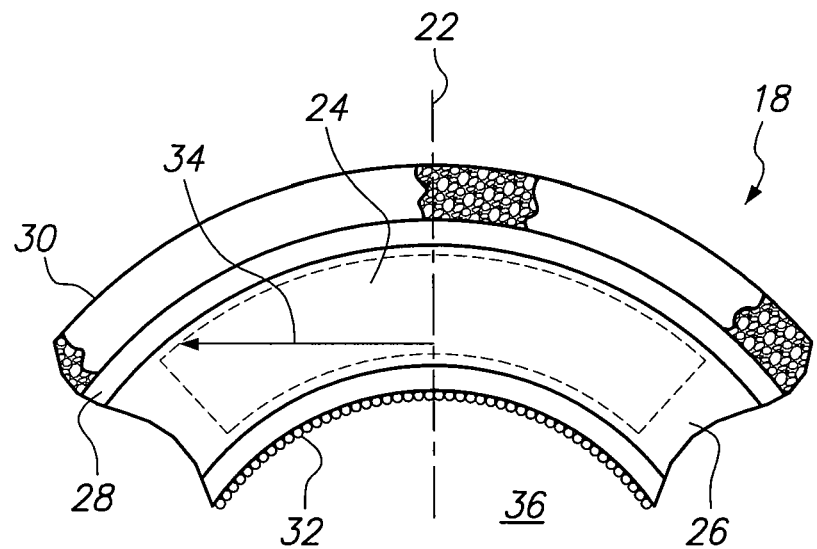
FIG. 2 is a cross sectional view of the cornea of an eye.

Referring now to FIG. 2, a cross-section of a cornea 18 is shown with a representative visual axis 22. Although the visual axis 22 will be unique for each cornea 18, it can, nevertheless, be accurately identified. Importantly, for ophthalmic laser surgery, the operation of system 10 must be conducted with reference to the visual axis 22. On the other hand, for a lamina of transparent material (i.e. material that is not a cornea 18) an axis similar to the visual axis 22 can be identified and defined for operational purposes.

As shown in FIG. 2, the present invention contemplates the identification of an operational volume 24 that is located completely within the stroma 26 of cornea 18. In general, the operational volume 24 extends from a predetermined distance below Bowman's capsule 28 (e.g. 8 microns) to a depth in the stroma 26 that is about 90% of the distance between the anterior surface 30 and the posterior surface 32 of the cornea 18 (e.g. approximately 450 microns). Further, the operational volume 24 extends through a radial distance 34 from the visual axis 22 that is equal to about four millimeters. As indicated above, it is important for purposes of ophthalmic laser surgery that the operational volume 24 be confined to tissue within the stroma 26. As will be appreciated by the skilled artisan, the operational volume 24 in the cornea 18 is influenced by pressure exerted against the cornea 18 by aqueous fluid in the anterior chamber 36.

Operation

Figure 3:
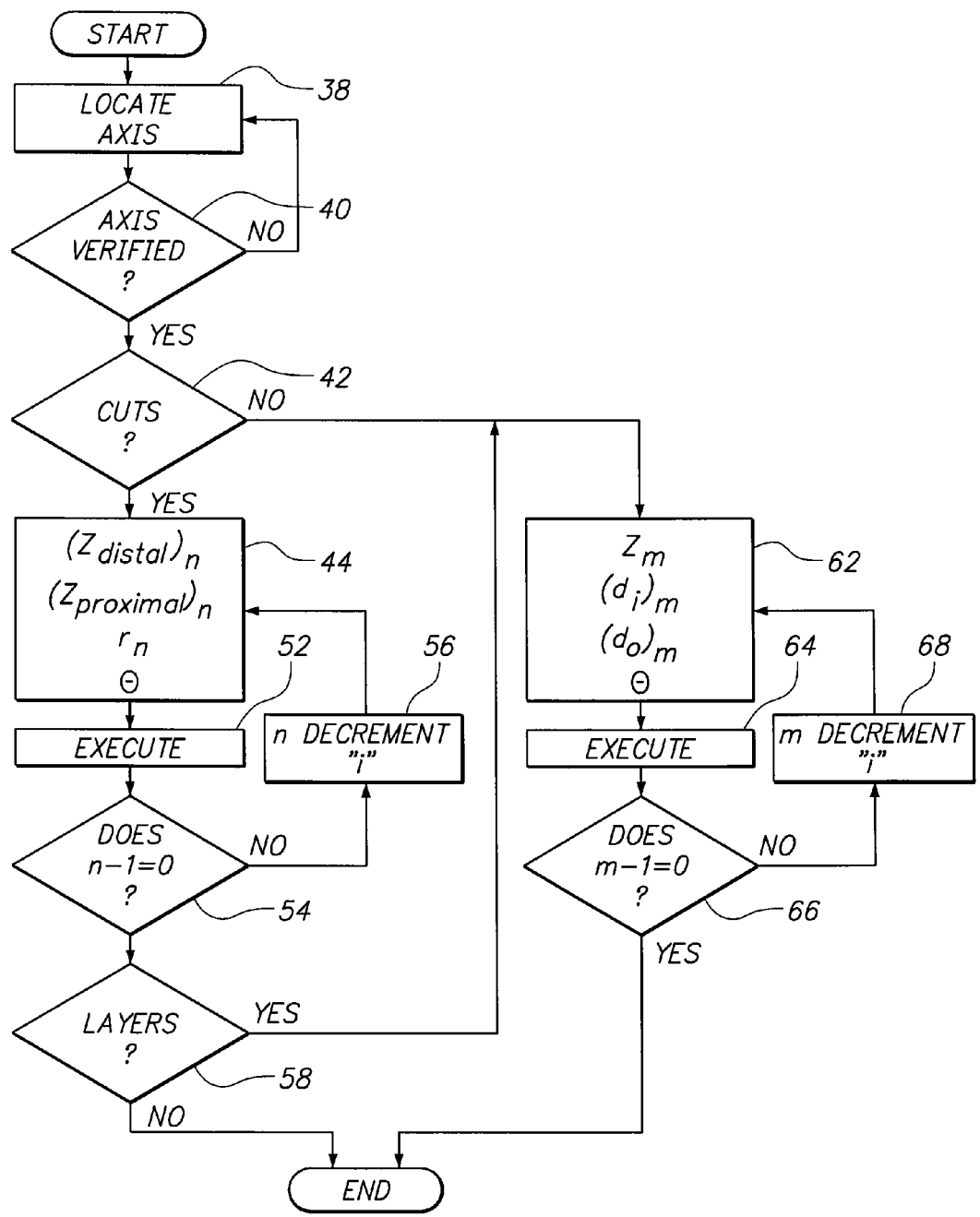
FIG. 3 is a logic chart showing a relationship of the steps in a methodology for use with the present invention.

For the operation of the system 10 of the present invention, the action block 38 in FIG. 3 indicates that the first task to be performed is the location of the axis 22. Specifically, in the case of ophthalmic laser surgery, the axis 22 will be a visual axis. On the other hand, for a lamina of transparent material (i.e. not tissue), the axis 22 can be defined as required. Typically, however, the axis 22 will be generally perpendicular to the lamina and, therefore, similar to the orientation of a visual axis 22 relative to a cornea 18.

Once the location of the axis 22 has been verified for the system 10 (see inquiry 40 in FIG. 3), it is necessary for the computer 12 to determine whether "cuts" or "layers" are to be created by LIOB. If inquiry 42 indicates that "cuts" are to be made, the computer 12 retrieves the appropriate input parameters 20 in accordance with action block 44. In this case, the input parameters 20 will include $(z_{distal})_n$, $(z_{proximal})_n$, radius "$r_n$" and an azimuthal angle θ. Specifically, $(z_{distal})_n$ and $(z_{proximal})_n$ are established at different distances from a same datum (see FIG. 4). And, the radius "$r_n$" is selected at a distance from the axis 22, while the azimuthal angle θ is measured around the axis 22. With these input parameters 20, the system 10 can then perform LIOB on either cylindrical cuts 46 (see FIG. 4) or radial cuts 48 (see FIG. 5).

Figure 4:
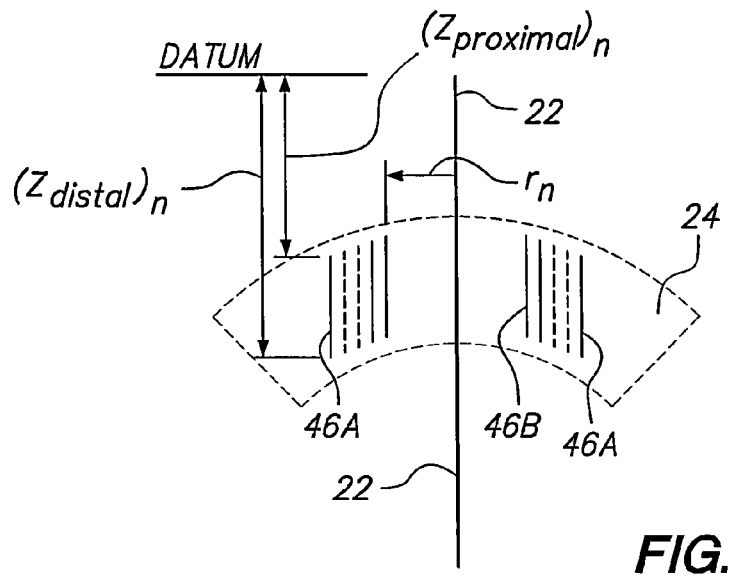
FIG. 4 is a schematic presentation of an operational volume in accordance with the present invention showing parameters for the creation of cylindrical cuts.

In FIG. 4, the cylindrical cuts 46a and 46b are only exemplary. For these cylindrical cuts 46a and 46b, as with others, each will have its own $(z_{distal})_n$, and its own $(z_{proximal})_n$. As indicated there can be an "n" number of cylindrical cuts 46, but all must be centered on the visual axis 22. Thus, the cuts 46 will be parallel to each other and also parallel to the axis 22. If the radius "$r_n$" is constant, the cylindrical cuts 46 will be circular cylindrical cuts 46. On the other hand, if the radius "$r_n$" is varied along an oval path, the cylindrical cuts 46 will be elliptical cylindrical cuts 46. Further, the azimuthal angle θ can extend through a complete 360° arc or be divided into desired segments. As intended for the system 10 of the present invention, the azimuthal angle θ is measured from a common base line 50 (see FIG. 5).

Figure 5:
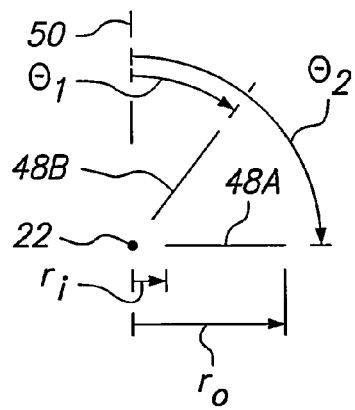
FIG. 5 is a schematic presentation showing parameters for the creation of radial cuts.

With reference to FIG. 5 it will be appreciated that when a constant azimuthal angle θ is selected and maintained, while the radius "$r_n$" is allowed to change through a pre-selected range between an inner radius "$r_i$" and an outer radius "$r_o$", radial cuts 48 can be created. Specifically, as shown in FIG. 5, the radial cut 48a is made at an azimuthal angle $\theta_2$, and the radial cut 48b is made at an azimuthal angle $\theta_1$.

Returning to FIG. 3 the creation of cylindrical cuts 46 and radial cuts 48 are accomplished individually as indicated by action block 52. After the creation of each cut 46 or 48, however, the system 10 determines whether additional cuts 46 or 48 are to be made. To do this, inquiry 54 specifically questions whether all "n" cuts 46 or 48 have been made. If not, action block 56 decrements "n" and action blocks 44 and 52 create an additional cut 46 or 48 in accordance with appropriate remaining input parameters 20. Preferably, in the case of cylindrical cuts 46, there will be a separation distance of about two hundred microns between adjacent cuts 46.

Figure 6:
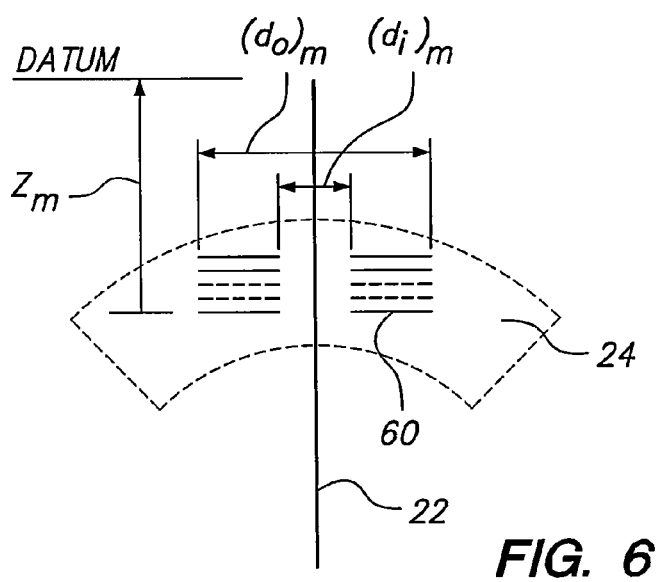
FIG. 6 is a schematic presentation of an operational volume in accordance with the present invention showing parameters for the creation of layers.

After all of the desired cylindrical cuts 46 or radial cuts 48 have been made, inquiry 58 questions whether the system 10 requires the creation of layers 60 (see FIG. 6). If not, operation of the system 10 is ended. On the other hand, if layers 60 are to be created, the operation of the system 10 proceeds to action block 62 where additional input parameters 20 are input to the computer 12. At this point, it is to be noted that if inquiry 42 had indicated that no cylindrical cuts 46 or radial cuts 48 were to be made, the operation of system 10 would have proceeded directly to action block 62 at that time. In either case, the input parameters 20 for use in the creation of layers 60 include a depth into the operational volume 24 "$z_m$", an inner diameter $(d_i)_m$, an outer diameter $(d_o)_m$ and, again, an azimuthal angle θ.

In FIG. 6, it can be seen that an "m" number of layers 60 can be created. Specifically, with a depth "$z_m$" individually selected for each layer 60, the diameters $(d_i)_m$ and $(d_o)_m$ can also be selected to create the layer 60 as an annulus (i.e. $d_i > 0$) or as a disk (i.e. $d_i = 0$). After the creation of each layer 60, the system 10 determines whether additional layers 60 are to be made. To do this, inquiry 66 specifically questions whether all "m" layers 60 have been made. If not, action block 68 decrements "n" and action blocks 62 and 64 create an additional layer 60 in accordance with appropriate remaining input parameters 20. Further, as with the cuts 46 and 48 discussed above, the azimuthal angle θ for layers 60 can be a complete 360° arc, or be in segments. Preferably, the separation distance between adjacent layers 60 will be about ten microns.

Once all of the cylindrical cuts 46, radial cuts 48 and layers 60 have been created as indicated for the present invention, operation of the system 10 is ended.

While the particular Computer Control for Bio-Mechanical Alteration of the Cornea as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for controlling a laser beam to perform an intrastromal ophthalmic surgical procedure to alter the shape of a transparent lamina in an eye, the method comprising the steps of:

electronically connecting a computer with a laser unit;

identifying an axis substantially perpendicular to the lamina, wherein the axis establishes a reference datum for movement of the laser beam;

creating a predetermined computer program for directing the laser unit to make a first surface enclosed within the lamina in accordance with requirements of the surgical procedure and a second surface unconnected with the first surface, wherein the surfaces are substantially parallel, and are defined relative to the axis to weaken the lamina;

determining cutting parameter coordinates for each of the surfaces;

entering the cutting parameter coordinates into the computer, wherein the cutting parameter coordinates are defined relative to the axis;

generating a laser beam with the laser unit;

focusing the laser beam to a focal spot in the lamina; and moving the focal spot in accordance with the cutting parameters, to perform Laser Induced Optical Breakdown (LIOB) over each defined surface inside the lamina, and wherein said first surface and said second surface each have a thickness of approximately two microns to weaken the lamina and alter the shape of the lamina in response to forces imposed on the eye parallel to the axis.

2. A method as recited in claim 1 further comprising the step of inputting cutting parameters to the computer for the first and second surfaces, wherein the parameters define portions of each surface for LIOB.

3. A method as recited in claim 2 wherein the cutting parameters include a location for a distal end of the first surface $(Z_{distal})_n$ wherein "n" identifies the surface, a location for a proximal end of the first surface $(Z_{proximal})_n$, a radius "$r_n$" measured from the axis, and an azimuthal angle θ measured around the axis from a base line.

4. A method as recited in claim 3 wherein the azimuthal angle θ is constant, and the radius "$r_n$" is varied through a range of approximately three millimeters to create a radial cut.

5. A method as recited in claim 3 wherein each defined surface is a cylindrical curved surface and each cylindrical curved surface is centered on the axis.

6. A method as recited in claim 5 wherein the radius "$r_n$" is constant to create a circular cylindrical curved surface.

7. A method as recited in claim 1 further comprising the step of selectively moving the focal spot in accordance with the predetermined computer program for the LIOB of material on the first and second surfaces comprising annular shaped layers in the lamina, wherein each layer is centered on the axis, and the LIOB of the material results in a layer having a thickness of approximately two microns, and further wherein adjacent layers are approximately ten microns distant from each other.

8. A method as recited in claim 7 further comprising the step of inputting layer parameters to the computer, wherein the layer parameters define portions of the layers for LIOB.

9. A method as recited in claim 8 wherein the layer parameters include an axial location for each layer $Z_m$ wherein "m" identifies the layer, an inner diameter $(d_i)_m$, an outer diameter $(d_o)_m$, and an azimuthal angle θ measured around the axis.

10. A computer program product for use with a computer for controlling a laser beam to perform an intrastromal ophthalmic surgical procedure on tissue in the cornea of an eye, wherein the computer program product comprises program sections for respectively:
electronically connecting the computer with a laser unit;
identifying a visual axis for the eye, wherein the axis establishes a reference datum for movement of the laser beam during the surgical procedure;
programming the laser unit to perform Laser Induced Optical Breakdown (LIOB) over a first surface enclosed within the cornea in accordance with requirements of the surgical procedure and a second surface unconnected with the first surface, wherein each surface is programmed to weaken the cornea, and each is defined relative to the axis;
determining cutting parameter coordinates for each the first and second surfaces;
entering the cutting parameter coordinates into the computer, wherein the cutting parameter coordinates are defined relative to the axis;
generating a laser beam with the laser unit;
focusing the laser beam to a focal spot in the cornea; and
moving the focal spot in accordance with the predetermined computer program in the computer to perform Laser Induced Optical Breakdown (LIOB) over the first and second surfaces inside the cornea, wherein the first and second surfaces are substantially parallel and wherein each of the first and second surfaces has a thickness of approximately 2 microns to weaken the cornea over the surface and alter the shape of the cornea in response to forces imposed on the eye parallel to the axis.

11. A computer program product as recited in claim 10 further comprising a program section for inputting cutting parameters to the computer for the first and second surface, wherein the cutting parameters define portions of each of the first and second surfaces for LIOB and include a location for a distal end of each surface $(Z_{distal})_n$ wherein "n" identifies the particular surface, a location for a proximal end of each surface $(Z_{proximal})_n$, a radius "$r_n$" measured from the axis, and an azimuthal angle θ measured around the axis from a base line.

12. A computer program product as recited in claim 11 wherein the azimuthal angle θ is constant, and the radius $(r_c)_n$ is varied through a range of approximately three millimeters to create a radial cut.

13. A computer program product as recited in claim 11 wherein each of the first and second surfaces is a cylindrical curved surface and each cylindrical curved surface is centered on the axis.

14. A computer program product as recited in claim 11 wherein the program section for moving the focal point further comprises selectively moving the focal spot over the first and second surfaces in accordance with the predetermined computer program for the LIOB of material on a plurality of annular shaped layers in the cornea, wherein each layer is centered on the axis, and the LIOB of the material results in a layer having a thickness of approximately two microns, and further wherein the adjacent layers are approximately ten microns distant from each other.

15. A computer program product as recited in claim 14 further comprising a program section for inputting layer parameters to the computer, wherein the layer parameters define portions of the layers for LIOB and include an axial location for each layer $Z_m$ wherein "m" identifies the particular layer, an inner diameter $(d_i)_m$, an outer diameter $(d_o)_m$, and an azimuthal angle θ measured around the axis.

16. A system for controlling a laser beam during an ophthalmic surgical procedure to alter the shape of a transparent lamina, the system comprising:
a laser unit for generating and focusing a laser beam to a focal spot in the lamina;
a predetermined computer program for use with an identified axis substantially perpendicular to the lamina, wherein the axis establishes a reference datum for movement of the laser beam during the surgical procedure, and for directing the laser unit to make a first surface and a second surface unconnected, and substantially parallel, with the first surface, the first and second surfaces enclosed within the lamina by moving the focal spot of the laser beam in accordance with cutting parameter coordinates relative to the axis, wherein the first and second surfaces are selected in accordance with requirements of the surgical procedure to weaken the lamina; and
a computer connected to the laser unit for moving the focal spot in accordance with the predetermined computer program, and relative to the axis, to perform Laser Induced Optical Breakdown (LIOB) over each of the first and second surfaces inside the lamina, wherein each of the first and second surfaces has been defined relative to the axis by coordinates for the predetermined program and wherein each of the first and second surfaces has a thickness of approximately two microns to weaken the lamina over the surface and alter the shape of the lamina in response to forces imposed on the lamina parallel to the axis.

17. A system as recited in claim 16 wherein the predetermined computer program operates with cutting parameters for the first and second surfaces and the parameters for each surface of the first and second surfaces include a location for a distal end of each surface $(Z_{distal})_n$ wherein "n" identifies the particular surface, a location for a proximal end of each surface $(Z_{proximal})_n$, a radius "$r_n$" measured from the axis, and an azimuthal angle θ measured around the axis.

18. A system as recited in claim 16 wherein each of the first and second surfaces is cylindrical and is centered on the axis.

19. A system as recited in claim 16 wherein the predetermined computer program moves the focal spot in accordance with the predetermined computer program for the LIOB of material on a plurality of annular shaped layers in the lamina, wherein each layer is centered on the axis, and the LIOB of the material results in a layer having a thickness of less than approximately two microns, and further wherein the adjacent layers are approximately ten microns distant from each other.

20. A system as recited in claim 19 wherein the predetermined computer program operates with layer parameters including an axial location for each layer $Z_m$ wherein "m" identifies the layer, an inner diameter $(d_i)_m$, an outer diameter $(d_o)_m$, and an azimuthal angle θ measured around the axis.

\* \* \* \* \*